United States Patent [19]

Dubrul et al.

[11] Patent Number: 4,834,703
[45] Date of Patent: May 30, 1989

[54] LIPOSUCTION FILTER AND LIPOPLASTY DEVICE

[76] Inventors: Will R. Dubrul, P.O. Box 1211, Santa Barbara, Calif. 93103; Martin P. Elliott, 250 Hazel Dr., Corona Del Mar, Calif. 92625

[21] Appl. No.: 124,286

[22] Filed: Nov. 23, 1987

[51] Int. Cl.$^4$ .......................................... A61M 31/00
[52] U.S. Cl. ..................................................... 604/48
[58] Field of Search ......................... 210/130, 407, 40; 55/296, 297, 313; 604/31, 35, 40, 48, 164, 184, 190, 275, 406, 38

[56] References Cited

U.S. PATENT DOCUMENTS

| | | | |
|---|---|---|---|
| 2,239,868 | 4/1941 | Williams | 210/130 |
| 2,768,754 | 10/1956 | Briggs | 210/130 |
| 2,895,613 | 7/1959 | Griffiths | 210/130 |
| 4,710,162 | 12/1987 | Johnson | 604/51 |
| 4,744,789 | 5/1988 | Johnson | 604/218 |

FOREIGN PATENT DOCUMENTS 68445  5/1914  Switzerland ......................... 55/296

Primary Examiner—Stephen C. Pellegrino
Assistant Examiner—J. L. Kruter
Attorney, Agent, or Firm—Michael G. Petit

[57] ABSTRACT

A in-line device for the aseptic collection and treatment of tissue aspirate comprising a cartridge housing a removable filter is described. The device provides filter means for removing desired cells from a crude tissue aspirate, a rake for scraping the cells from the surface of the filter and a pressure relief valve to divert the flow of aspirate when the filter capacity is exhausted. With the filter and rake removed the outer cartridge also serves as the barrel of a syringe for further transfer of harvested cells.

2 Claims, 1 Drawing Sheet

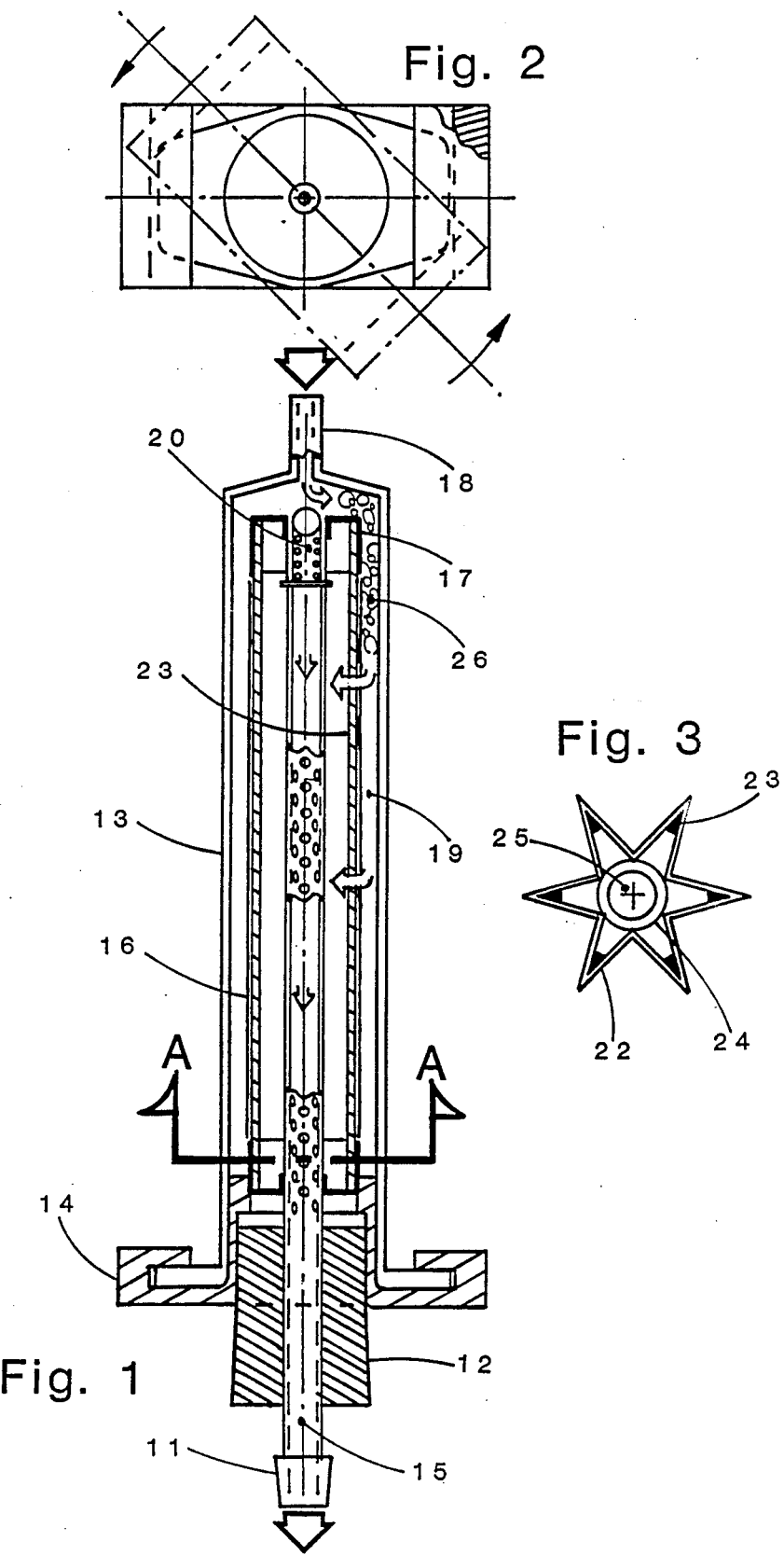

LIPOSUCTION FILTER AND LIPOPLASTY DEVICE

SUMMARY

A device is described for the harvesting, washing, and reinjection of adipose cells for lipoplasty. The device provides for in-line connection to conventional vacuum equipment and comprises a cartridge housing a removable filter and rake, a filter and filter bypass channel, an automatic pressure relief valve in line with the filter bypass channel and a plunger for reinjection of harvested, washed cells into the donor.

FIELD OF THE INVENTION

The invention provides a sterilizable device for the harvesting, washing and reinjection of aspirated tissue cells. The device is described for use in plastic surgery, particularly lipoplasty, but may be used in other applications requiring collection, treatment, and reinjection or other transfer of tissue aspirate under sterile conditions.

BACKGROUND OF THE INVENTION

Lipoplasty refers to the injection of fat cells to recontour tissue. If the fat cells that are injected are derived from the patient's adipose tissue (an autograph), problems of immune response that can occur when animal foreign protein, such as collagen, is injected are avoided. The technique, although lacking FDA approval, has been used by plastic surgeons for at least thirty years. Newman reports using autogenous fat grafts to correct facial wrinkles, lines, furrows, congenital and developmental defects, and to effect cheek and chin enhancement or augmentation (Journal of Cosmetic Surgery, Vol. 3., No. 2., page 67 (1986)).

While a wide variety of techniques are currently in use for affecting lipoplasty, a single example may serve to clarify the salient features of the procedure. A local anesthetic is administered to the patient in sufficient quantity to perfuse the area from which fat cells are to be removed. A cannula, usually a 14 gauge or smaller needle, is inserted through the skin into the fatty tissue and a vacuum applied. The tip of the cannula is moved back and forth to assist with mechanical disruption of tissue. The aspirate; a heterogeneous mixture of blood and fat cells, is collected in a trap. The aspiration of fat cells may be preceded by an injection of saline or adrenalin to facilitate transport of disrupted fat cells through the lumen of the cannula.

The crude aspirate in the trap may then be either reinjected directly into the desired site or it may be processed to remove undesired components prior to reinjection. The readied aspirate is then transferred to a syringe and reinjected into a previously anesthetized recipient site.

Contamination of the aspirate during collection, processing or reinjection can result in cellulitis. To reduce the possibility of introducing exogenous microorganisms into the aspirate it is desirable to minimize handling and transfer of the aspirate. It is therefore an object of the present invention to provide a sterilizable device which can be used to trap, process and reinject aspirate tissue cells without the need for transfer. It is a further object of this invention to provide a device for collection and treatment of tissue aspirate prior to introduction into a tissue culture medium. The present invention can be best described by referring now to the figures.

BRIEF DESCRIPTION OF THE INVENTION

The invention is designed to operate in-line with standard tissue aspiration vacuum equipment. Crude tissue aspirate enters the device through a lumen in fluid contact with the lumen of the cannula. The aspirate entering the device is diverted by means of a valve to pass over the surface of a filter housed within the outer cartridge. When the accumulation of retentate on the filter surface is sufficient to substantially clog the filter pores it causes a pressure drop across the diversion valve. The diversion valve opens the filter bypass channel and permits a portion of the incoming crude aspirate to flow directly through the device toward the vacuum effectively bypassing the filter.

The filter, with cells separated from the crude aspirate adhering to its surface, is then withdrawn from the cartridge by pulling it through a rake of mating cross section to the filter. The rake scrapes the cells off of the filter surface as the filter is withdrawn where they fall into the outer cartridge. When the filter has been completely removed, the rake is removed from the outer cartridge and a plunger of mating cross section with the inner surface of the outer cartridge is inserted into the outer cartridge to form a syringe. The collected cells may then be reinjected into a prepared recipient site in the donor or placed in a suitable culture medium for further modification or investigation.

When the filter bypass valve opens, causing further tissue aspirate to pass directly toward the vacuum, the operator may remove the collection cannula and immerse the cannula in a sterile washing solution of lower viscosity than the crude tissue aspirate. Owing to its lower viscosity, a portion of the washing solution will pass over the filter surface removing debris and filterable material from the adhering cells. The retentate cells may then be collected by withdrawing the filter through the rake and proceeding as previously described.

The entire unit, including the outer cartridge, filter, rake and plunger, is sterilizable and provides a convenient means for sterile harvesting and washing of cells for reinjection or further investigation.

FIGURES

FIG. 1. A cross sectional view of the Liposuction Filter/Lipoplasty device taken along the long axis.

FIG. 2. Schematic view of filter trap assembly and removal.

FIG. 3. Schematic and cross sectional view of rake.

DESCRIPTION OF THE PREFERRED EMBODIMENT

Referring now to FIG. 1, tissue aspirate enters the outer cartridge (13) through the intake port (18) under the force of a vacuum (not shown) applied to the exhaust port (11). The aspirate entering through the intake port (18) encounters the ball valve (20) and is diverted to pass through the filter channel (19).

As the crude tissue aspirate passes through the filter channel (19) the pressure drop across the filter surface (16) causes filtrate to pass through the filter (16) and porous filter support (23) into the filter bypass channel (15) where it continues to flow in the direction of the exhaust port (11). Material in the tissue aspirate that is too large to pass through the filter pores (the retentate) adheres to the surface of the filter (16).

As the retentate (26) builds up on the surface of the filter (16) the pressure drop across the filter surface (16) increases until the differential pressure between the filter channel and the filter bypass channel overcomes the restoring force of the ball valve's restraining spring and opens the filter bypass channel (15). As the ball valve opens, the flow of aspirate is partitioned between the filter and filter bypass channel. A portion of the aspirate will continue to flow through the filter channel until the filter is completely clogged. When this occurs, all subsequent aspirate will flow through the filter bypass channel (15). The filter retentate (not shown) is now ready for washing prior to reinjection.

When the filter becomes completely clogged by retentate, the ball valve (20) is in its fully open position. The cannula (not shown) may then be removed from the patient and immersed in a treatment solution of lower viscosity (not shown) hereinafter referred to as aspirate i. Aspirate i may be sterile saline for washing debris from retentate or it may be a solution containing an agent that modifies the retentate cells in a desired manner.

A rake (14) (FIG. 1) of mating cross section to the filter (16) is affixed to the exhaust port end (11) of the outer cartridge (13). The filter cross section is chosen to provide a large surface area for processing aspirate. In the preferred embodiment (FIG. 2b) the rake is a star shape with 6 points and 12 sides, in a pleated configuration surrounding the filter by pass channel and axially symmetric with both the filter bypass channel and the outer cartridge.

Following the aforesaid washing/pre-treatment of retentate cells, the filter assembly is withdrawn from the outer cartridge by pulling it through the rake (14). As the filter surface passes the mating rake surface, the retentate cells are scraped into the outer cartridge. When the filter assembly has been completely withdrawn from the device, the rake is rotated as shown in FIG. 2 to disengage a locking flange, removed and a sterile plunger inserted into the barrel of the outer cartridge. The treated retentate cells are ready for either reinjection into the donor or transfer to a sterile culture medium for further investigation.

What we claim is:

1. An in-line device for separating and trapping cells from a crude mixture of donor mammalian tissue aspirated by means of a vacuum through a cannula comprising:
   a. an outer cartridge with intake and exhaust ports affixed thereto and a filter channel and a filter bypass channel passing therethrough;
   b. pressure responsive means for switching the flow of tissue aspirate through the cartridge between the filter channel and the filter by-pass channel;
   c. a filter;
   d. means for removing cells from the filter;
   e. means for the subcutaneous reinjection of said cells into the donor.

2. The device of claim 1 wherein said means for reinjection comprises a plunger of mating cross section with the interior cross section of said cartridge.

* * * * *